United States Patent [19]

Vaughan, Jr. et al.

[11] 4,422,941

[45] Dec. 27, 1983

[54] APPARATUS FOR LIQUID-SOLID COLUMN CENTRIFUGATION CHROMATOGRAPHY AND METHOD

[75] Inventors: Maurice H. Vaughan, Jr., Pittsburgh, Pa.; Klaus B. Andersen, Copenhagen, Denmark

[73] Assignee: University of Pittsburgh, Pittsburgh, Pa.

[21] Appl. No.: 185,335

[22] Filed: Sep. 8, 1980

[51] Int. Cl.$^3$ .......................................... B01D 15/08
[52] U.S. Cl. .................................. 210/657; 210/198.2
[58] Field of Search ................... 210/656, 657, 198.2; 55/386; 233/28, 14 A

[56] References Cited

U.S. PATENT DOCUMENTS

| | | | |
|---|---|---|---|
| 2,877,861 | 3/1959 | Miller | 55/73 |
| 2,967,148 | 3/1961 | Karnofsky | 208/310 |
| 3,078,647 | 2/1963 | Mosier | 55/197 |
| 3,113,103 | 12/1963 | Lowery | 210/198.2 |
| 3,194,400 | 7/1965 | Herndon | 210/198.2 |
| 3,201,921 | 8/1965 | Heyes | 55/56 |
| 3,237,855 | 3/1966 | Anderson | 233/28 |
| 3,244,363 | 4/1966 | Hein | 233/28 |
| 3,250,395 | 5/1966 | Blume | 210/198.2 |
| 3,395,093 | 7/1968 | Liberti | 204/301 |
| 3,417,548 | 12/1968 | Thompson | 55/197 |
| 3,440,864 | 4/1969 | Blume | 73/61.1 |
| 3,527,350 | 9/1970 | Tuthill et al. | 210/198.2 |
| 3,583,230 | 6/1971 | Patterson | 73/422 |
| 3,617,557 | 11/1971 | Giltrow | 210/657 |
| 3,664,845 | 5/1972 | Friedman | 99/57 |
| 3,666,105 | 5/1972 | Fox | 210/198.2 |
| 3,775,309 | 11/1973 | Ito et al. | 210/657 |
| 3,810,545 | 5/1974 | Filz et al. | 210/198.2 |
| 3,856,669 | 12/1974 | Ito et al. | 210/657 |
| 3,925,207 | 12/1975 | Scriba | 210/138 |
| 3,994,805 | 11/1976 | Ito | 210/657 |
| 3,997,105 | 12/1976 | Hayden et al. | 233/26 |
| 4,051,025 | 9/1977 | Ito | 210/657 |
| 4,077,886 | 3/1978 | Fukuda et al. | 210/657 |
| 4,082,217 | 4/1978 | Westberg | 233/25 |
| 4,228,009 | 10/1980 | Ito | 210/198.2 |
| 4,243,534 | 1/1981 | Bulbenko | 210/656 |

OTHER PUBLICATIONS

Emneus, A Procedure for Gel Filtration of Viscous Solutions, J. Chromatog 32 (1968) 243-257.
Krieger et al., Micro-Step-Exclusion Chromatography, Analytical Biochemistry 81, 450-453 (1977).
Neal et al., A Rapid Method for Desalting Small Volumes of Solution, Anal. Chem. 55, 328-330 (1973).

Primary Examiner—John Adee
Attorney, Agent, or Firm—Buell, Blenko, Ziesenheim & Beck

[57] ABSTRACT

Centrifugation chromatography columns including column members for containing a particle bed and a porous member underlying the bed. The column members have an upper receiving opening and a lower discharge opening. A receptacle is demountably secured to the column. Attachment is effected through cooperation between a lower portion of the column members and an upper portion of the receptacles. Support structures may be provided on the exterior of the column members to facilitate support thereof by a centrifuge. In another embodiment of the invention continuous column centrifugation chromatography is provided by means of a column rotor on which are mounted a plurality of columns. A collector rotor is provided with means for receiving material discharged from the columns. Relative synchronized movement between the column rotor and the collector rotor is provided. A distribution system for supplying liquid to be separated to the columns on a continuous basis is provided. Funnel means may be employed to facilitate transfer of effluent from the column to the collector rotor. A method for continuous column centrifugation chromatography employing a rotating array of columns which are subjected to a centrifugal force, effecting synchronized movement of an array of receptacles positioned to receive the liquid discharged from the columns and supplying on a continuous basis liquid to the columns.

22 Claims, 33 Drawing Figures

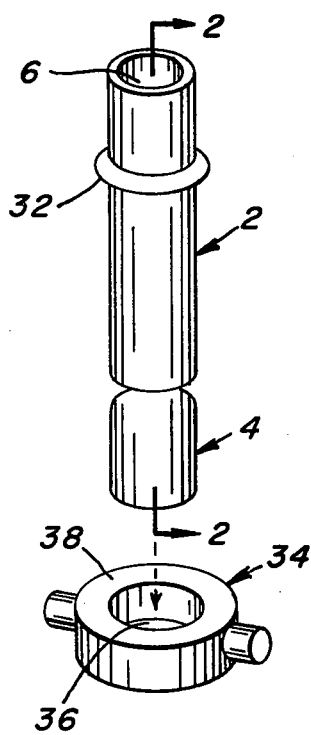
FIG. 1.
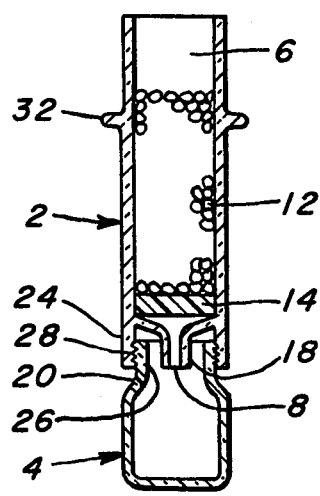
FIG. 2.
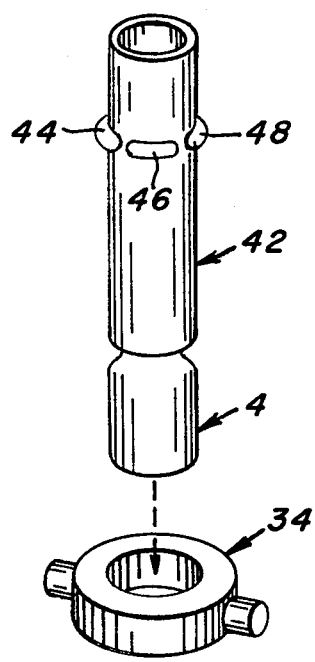
FIG. 3.
FIG. 4.
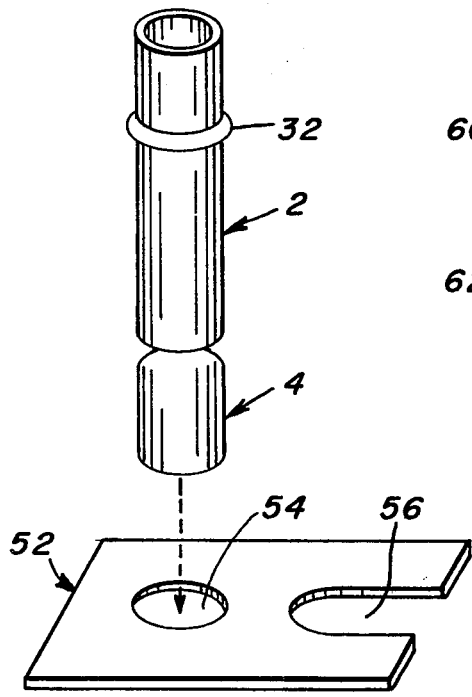
FIG. 5.
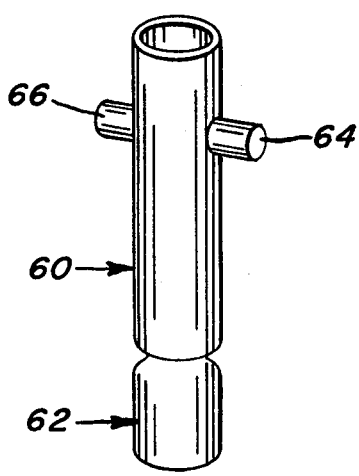
FIG. 6.
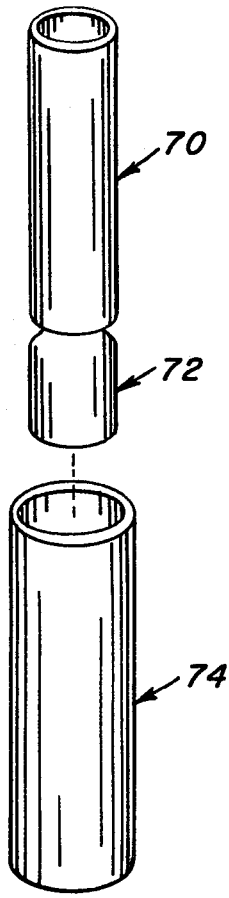

APPARATUS FOR LIQUID-SOLID COLUMN CENTRIFUGATION CHROMATOGRAPHY AND METHOD

BACKGROUND OF THE INVENTION

1. Field of the Invention

This invention relates to apparatus and methods for liquid-solid column centrifugation chromatography including automated, continuous systems therefor.

2. Description of the Prior Art

Chromatography is an analytical and preparative chemical process which separates molecules from each other according to their various physical and chemical properties, including their molecular size, electric charge and tendency to adsorb to various specific surfaces. This method is widely used throughout the chemical and medical sciences in research work, clinical laboratories and industry, both to analyze mixtures of chemicals and to purify specific chemcals. Liquid-solid chromatography involves the chromatography of molecules dissolved in liquids which are passed over beds of particles. When the particles are contained in a column, a porous plate is generally placed at the bottom and the particle bed is packed thereover. The porous plate serves to support the particle bed while allowing liquid to flow through the column and bed.

Among the problems which exist with known types of liquid-solid chromatography, such as gel filtration or permeation chromatography is the fact that the technique is frequently unduly time consuming. Also, the process frequently leads to undesirable dilution of the molecules being chromatographed.

It has previously been suggested to employ the centrifuge in chromatography.

It has been suggested to employ centrifugal gel filtration methods in connection with basket centrifuges. See "A Procedure for Gel Filtration of Viscous Solutions" by N. I. Arne Emneus, 32 Journal of Chromatography, pages 243-257 (1968). Other disclosures of the use of a centrifuge in chromatography as well as tube construction and methods are found in "A Rapid Method for Desalting Small Volumes of Solution" by Neal and Florini, 55 Analytical Biochemistry, pages 328-330 (1973) and "Micro-Step-Exclusion Chromatography" by Krieger and Tobler, 81 Analytical Biochemistry, pages 450-453 (1977).

U.S. Pat. No. 3,583,230 discloses sample injection methods and apparatus. The injector has an inlet opening which communicates with a central channel provided with chromatographic filter material and a capillary outlet. It is noted, however, the injection of the liquid samples into the column is for subsequent chromatographic development without use of centrifugation.

U.S. Pat. No. 3,440,864 discloses liquid chromatographic columns with a threaded jacket. The system is not designed for centrifugal chromatography.

U.S. Pat. No. 3,664,845 discloses the use of a bed of molecular fractionating gel under the influence of a centrifugal force such that the bed is expanded and contracted by means of pulsed centrifugation.

It has been known to attempt various means for automating chromatography. U.S. Pat. No. 3,194,400 relates to a liquid chromatographic centrifuge wherein a rotor cooperates with radial channels which are provided with separate media. The disc 20 is provided with radial channels 40. After centrifugation, the various zones are examined to determine different zones of chemical fractions. These zones may then be separately eluted from portions of the sheet. The receptacles provided are intended to receive solvent liquid flowing from the sheet, but generally this liquid would not be collected in discrete fractions. The resolved chemicals stay on the sheet.

While not involving centrifugation chromatography in columns, U.S. Pat. No. 3,395,093 discloses separations which are carried out on a disc of paper or gel under the dual influence of centrifugal and electrical forces. Structure for handling the materials is disclosed.

U.S. Pat. No. 3,666,105 discloses continuous liquid-solid chromatography employing a pair of cylinders which cooperate to define a column. It is noted that the fraction collector rotates with the column as a result of the design.

A number of other disclosures suggest the use of discs. U.S. Pat. No. 4,077,886 employs discs and makes no provision for collection of the resolved components into eluted fractions for analysis and subsequent use. U.S. Pat. No. 3,417,548 discloses the use of a pair of spaced discs. U.S. Pat. No. 3,527,350 discloses centrally introduced flow and resolution within a disc bed. U.S. Pat. No. 3,617,557 discloses continuous centrifugation chromatrography in a disc material. Under the influence of Coriolis forces, different separated components come to different regions of the rim of the disc. Cups are provided to receive eluate from discrete regions of the rim. U.S. Pat. No. 3,201,921 discloses selective treatment of a fluid by adsorption. Pumping action is the primary moving force for the liquid which is fed in at least two zones with a plurality of cells being provided adjacent the periphery. U.S. Pat. No. 3,113,103 discloses the use of centrifugal force in the disc. No provision is made for elution of separated components and, as a result, no fraction collector is provided. Means are provided for loading of samples.

There remains, therefore, a significant need for effective apparatus for both batch and continuous liquid-solid column centrifugation chromatography which produces improved resolution in reduced time.

SUMMARY OF THE INVENTION

The present invention has solved the above-described problems by providing an effective means of improving liquid-solid column centrifugation chromatography.

In one embodiment of the present invention, column means are provided with a particle bed and an underlying porous member. The column means have downwardly depending first attaching means. Receptacle means are positioned under the column means and by means of second attaching means are demountably secured to the column means. Various means for effecting such demountable securement are disclosed. Also, support means for faclitating securement of the column meansreceptable means assembly in a centrifuge are provided.

In another embodiment of the invention, automated means for providing substantially continuous liquid-solid column centrifugation chromatography are provided. A column rotor means is rotarably mounted and has a plurality of centrifugation columns secured thereto. Coaxially mounted for synchronous rotation with the column rotor means is a collector rotor means having a plurality of receptacles adapted to receive fluid discharged from the columns. Power means established the synchronized movement of the column rotor means and collector rotor means. Distribution means provided to the columns a continuous supply of liquid to be separated.

The method of the present invention provides for continuous liquid-solid column centrifugation chromatography.

It is an object of this invention to provide a uniquely configured column-collection receptacle assembly for use in liquid-solid centrifuation chromatography.

It is a further object of this invention to provide such a column-receptacle combination wherein the receptacle is readily secured to and demounted from the overlying column member.

It is a further object of this invention to provide such a column-receptacle assembly which has means to facilitate securement thereof to a conventional centrifuge.

It is another object of the present invention to provide efficient systems for discontinuous and continuous liquid-solid column centrifugation chromatography.

It is another object of this invention to provide such apparatus which may be economically manufactured and efficiently employed.

It is another object of this invention to provide a method of automated liquid-solid column centrifugation chromatography.

These and other objects of this invention will be more fully understood from the following description of the invention on reference to the illustrations appended hereto.

BRIEF DESCRIPTION OF THE DRAWINGS

FIG. 1 is a schematic illustration of one embodiment of a column-receptacle assembly of this invention and associated retaining means.

FIG. 2 is a cross-sectional illustration of the assembly of FIG. 1 taken through 2-2.

FIGS. 3 and 4 are partially schematic perspective views showing other forms of column-receptacle assemblies and associated retaining members.

FIG. 5 is a further embodiment of the present invention showing a column-receptacle assembly.

FIG. 6 illustrates a schematic perspective view of another form of column-receptacle assembly along with retaining means.

DESCRIPTION OF THE PREFERRED EMBODIMENTS

Figure 7:
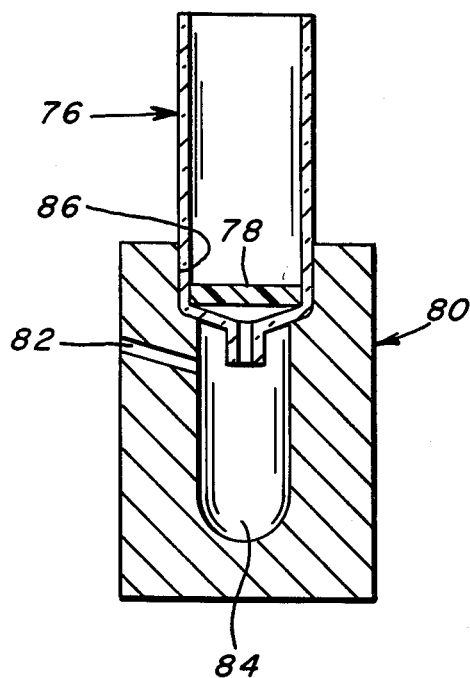
FIGS. 7 through 9 illustrate cross-sectional views of certain trunion constructions establishing column-receptacle assemblies.

In order to accomplish the objectives of the present invention, as conventional chromatography columns are not suited to use in a centrifuge, special column-receptacle assemblies are provided in the first embodiment of the present invention.

Referring now more specifically to FIGS. 1 and 2 there is shown a liquid-solid chromatography column assembly. The assembly consists of a column 2 under which is demountably secured a receptacle 4. The column 2 is provided with an upper liquid receiving opening 6 and a lower discharge opening 8. Within the column 2 is a bed 12 of chromatography bed material such as gel beads, for example, which is supported on a disc 14 which is adapted to resist passage of the bed material 12 therethrough, but permit the flow of liquid therethrough. The bed material may conveniently be any type suitable for use in liquid-solid chromatography. Examples of specific suitable materials are those sold under the trade designations Sephadex G-25 and G-50 (Pharmacia) or Bio-Gel P-4 and P-2 (Bio-Rad Laboratories). The discs 14 may conveniently be porous polyethylene discs.

In the form shown, the lower portion of column 2 has a pour spout 18 which defines discharge opening 8 which is in communication with the interior of receptacle 4. In order to facilitate flow into receptacle 4, at least one vent opening 20, which may conveniently be a hole of about 1/16 to 1/32 inch in diameter, is provided within the upper portion of the receptacle 4 so as to facilitate exhaust of air from the receptacle 4 while resisting discharge of fluid therefrom. If desired, in addition or in lieu of vent opening 20 in receptacle 4, a vent opening may be placed in the wall of column 2 in a portion in communication with the interior of receptacle 4. It could be placed in the region underlying the connection between pour spout 18 and the wall of column 2, for example. Also, venting could be effected by maintaining a column2—receptacle 4 connection, which is not air tight.

In effecting securement of the receptacle 4 in demountable underlying engagement with respect to the column, mechanical retention is provided in the embodiment shown in FIGS. 1 and 2. The lower portion of the column 2 has first attaching means 24 in the form of an annular tubular downward projection. The first attaching means 24 cooperate with second attaching means 26 on receptacle 4 which in the form shown consists of an upwardly projecting annular mouth portion. Cooperating treads 28 are provided on first attaching means 24 and second attaching means 26 in order to improve intimacy of securement.

The embodiment shown in FIGS. 1 and 2 provides means for securing the column-receptacle assembly rotatably within the rotor of a centrifuge. The upper portion of column 2 (within the upper one-half and preferably within the upper one-third of the axial length of the column) is provided with a substantially continuous exteriorly disposed rib 32. This rib 32 is preferably the portion of the column-receptacle assembly of greatest transverse dimension.

In the form shown in FIG. 1, a yoke member 34 which is adapted to be rotatably secured on the rotor of a centrifuge defines an opening 36 which will receive the column-receptacle assembly in such fashion that the annular rib 32 will not pass through opening 36, but preferably will rest on upper surface 38. The contact between annular rib 32 and surface 38 serves to resist undesired excessive passage of the column-receptacle assembly through opening 36.

The following will provide an example of how the apparatus of FIGS. 1 and 2 may be used in liquid-solid centrifugation chromatography in order to effect molecular separation. A column 2 of the type shown in FIGS. 1 and 2 without the receptacle 4 attached is provided with a slurry of chromatographic bed material in order to establish bed 12. Either prior to or after introduction of the slurry into the column 2, the column 2 is introduced into yoke 34 through opening 36 until annular rib 32 contacts upper surface 38. The column 2 is then subjected to centrifugal force in order to remove excess liquid from the slurry. The receptacle 4 is then secured in underlying position with respect to the column 2. A liquid sample containing molecules which will bind to the chromatographic bed material 12 and others which will not is introduced into the column 2 through opening 6. The column-receptacle assembly is then centrifuged with the nonbinding molecules being recovered in receptacle 4 in eluted liquid. The receptacle 4 containing the eluted liquid and non-binding molecules is then emptied and the receptacle 4 is then reattached to the column 2 or a different receptacle may be attached. A new solution which elutes the bound molecules is then introduced into the column through opening 6 and the column is centrifuged once again. This time the bound molecule is recovered in the elution solution. This final step may be repeated several times, if desired.

The prior art liquid-solid chromatography practice carried out in a bed of solid particles immersed in liquid has two principal problems which limit the speed at which the process can be performed. First of all, the liquid-filled spaces between the particles are usually very large in dimension compared to the size of the molecules being chromatographed. As a result, the liquid must be passed through the bed slowly if the molecules are to have an adequate chance to diffuse to the particle surfaces and interact with them. In addition, the flow of liquid through the bed must not be so rapid that uneven liquid flow across the bed developes due to hydrodynamic effects. Such uneven flow results in a decrease in the efficiency of separation of zones containing different types of molecules.

In the present system, by contrast, the liquid-filled particle bed is centrifuged prior to chromatography. As a result the liquid between those particles is largely removed leaving a thin layer of liquid on the surface of the particles in the bed in addition to the liquid which may permeate them. As the liquid layer on the centrifuge column particles is very small in thickness, it permits a very rapid equilibrium of molecules dissolved in it with the particles. In essence, the liquid layer is so thin that random diffusion becomes effective at promoting particle-molecule interaction. It, therefore, becomes advantageous to load a sample of molecules to be chromatographed in a column which has previously been centrifuged to remove free liquid. If this column is then centrifuged again after loading, the liqud sample moves down the particle bed in a thin layer itself, under conditions where interactions between the particles and the molecules being separated are maximized. As these interactions are so efficient in a thin layer of liquid, the flow rate down the column can be much higher than in conventional liquid-solid chromatography in a liquid-filled column. At the same time, there is very little problem with uneven liquid flow across the column bed because the bed is not filled with liquid. Instead, the liquid is flowing as a sheet over the bed particles. The result is that liquid-solid chromatography in a centrifuge column can accomplish the same type of separation as in normal, liquid-filled columns but much more rapidly, without sacrificing the ability to resolve different molecules efficiently. As very little free liquid is added to the column, the amount of dilution of the chromatographed molecules is very little.

Referring now to FIG. 3, another embodiment of the container-receptacle assembly adapted to cooperate with yoke 34 is illustrated. In this embodiment, the securement means consist of a series of segmented ribs 44, 46, 48 positioned within the upper third of the axial height of the column 42. The segmented ribs 44, 46, 48 serve to permit yoke 34 to support the column 42 and receptacle 4 against excessive penetration therethrough during centrifugation.

Referring to FIG. 4, there is shown a tube of the type shown in FIGS. 1 and 2 wherein the column-receptacle assembly may be employed without the need to use a yoke 34. In this embodiment of the flange 32 or an embodiment such as column 42 may be introduced directly into the rotor 52 by positioning the same within a hole 54 sufficiently small as to preclude the passage of annular rib 32 or rib segments 44, 46, 48 therethrough. Alternatively, the column-receptacle assemblies may be introduced into a slot 56 within a rotor.

Referring now to FIG. 5, the embodiment of column 60 and receptacle 62 assembly is provided with a pair of generally diametrically opposed outwardly projecting pins or lugs 64, 66. The pins or lugs 64, 66, may be used without a yoke so as to permit the column-receptacle assembly to pivot about a slot or other retaining means within the centrifuge rotor which rotatably secures pins or lugs 64, 66. Under the influence of centrifugal force, the column 60 will pivot about the pins 64, 66 to assume a position generally parallel to the centrifugal field.

In the embodiment illustrated in FIG. 6, the column 70 has a receptacle 72 demountably secured thereto with the column-receptacle assembly received within a trunion 74 which pivots on the rotor (not shown) of a centrifuge under the influence of centrifugal forces to bring the column to a position generally parallel to the centrifugal field.

While a vent opening 20 in order to facilitate efficiency of liquid transfer from the column 2 to receptacle 4 has been specifically shown in FIG. 2, for simplicity of disclosure, it will be understood that appropriate venting means will be provided in the columns, receptacles, or both in all embodiments of the present invention, but specific illustration and discussion of the vent opening will not be provided with respect to each embodiment as the form and positioning will be readily apparent to one skilled in the art.

In the embodiment shown in FIG. 7, a generally cylindrical column 76 is provided with a disc 78 which supports a chromatography bed (not shown). A trunion member 80 is provided with a vent passageway 82 disposed within the upper half of the trunion 80 and defines a liquid receiver portion 84 therewithin. The trunion 80 is provided with an annular undercut upper surface 86 which is in firm engagement with the lower portion of column 76 so as to establish the column-receptacle assembly.

Figure 8:
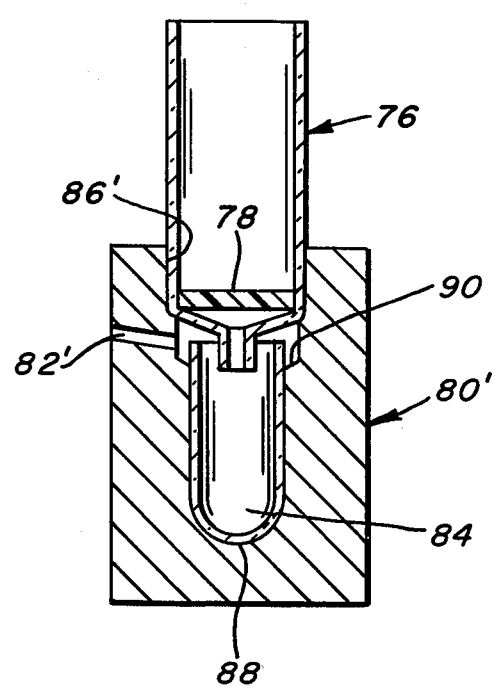

The embodiment of FIG. 8 is substantially identical with that of FIG. 7 except that the trunion 80' is provided with a step 90 positioned below the undercut upper surface 86 and a receptacle 88, which is removably secured within the trunion liquid receiver 84, is provided.

Figure 9:
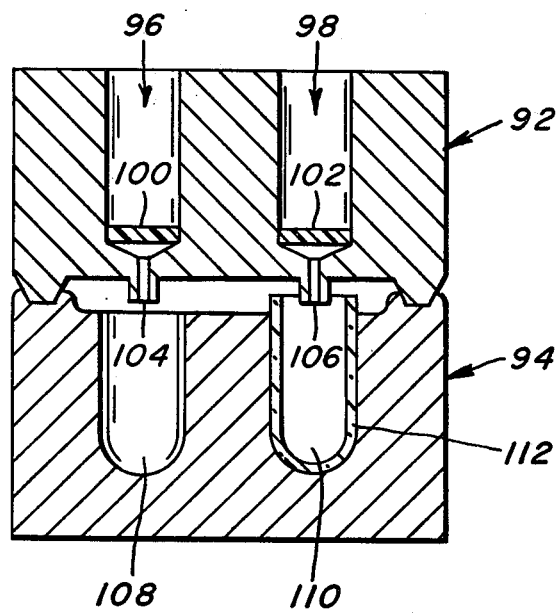

This invention also contemplates a single trunion member providing multiple columns or receptacles. Referring now to FIG. 9 there is shown in upper trunion member 92 and a lower trunion member 94. In the form shown, the upper trunion member 92 is provided with two columns 96, 98 which are integrally formed within the upper trunion member 92 and are provided respectively with discs 100, 102 and overlying chromatographic bed material (not shown). The columns 96, 98 are provided, respectively, with discharge outlets 104, 106 which are in overlying communicating relationship with receivers 108, 110 respectively. The receiver 110 is provided with a removable tube 112.

FIGS. 10 through 14 show examples of certain additional preferred embodiments of first and second attaching means for demountably securing an underlying receptacle to an overlying column.

Figures 10, 11, 12, 13, 14:
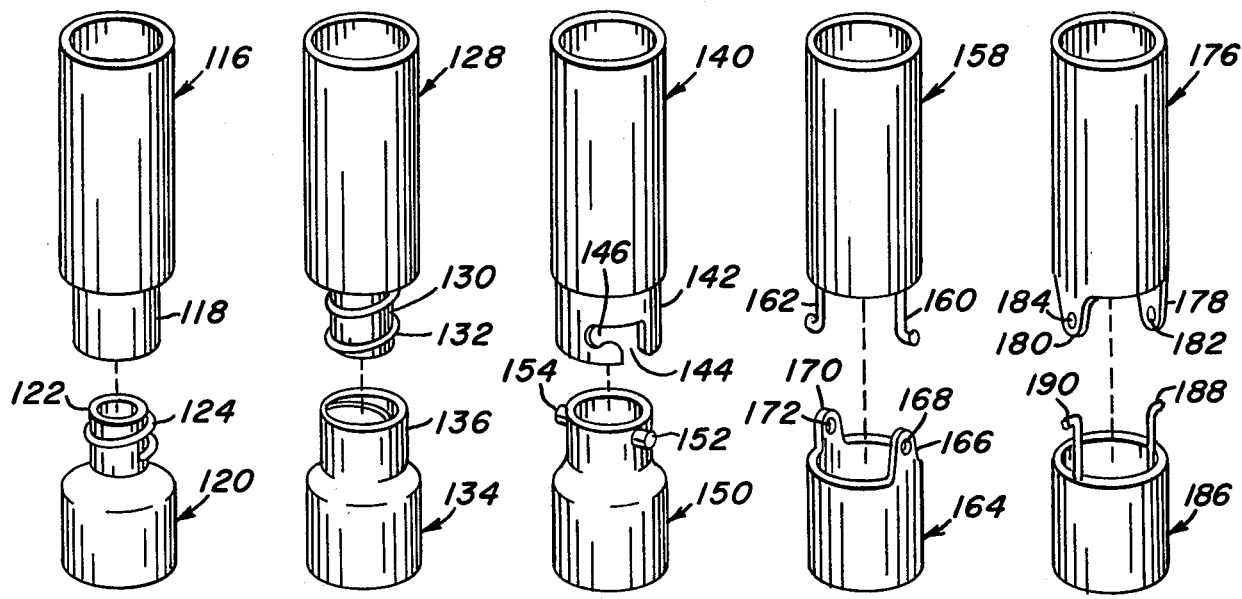
FIGS. 10 through 14 illustrate several types of attaching means for demountably securing the column to the receptacle.

In FIG. 10, column 116 has an upper generally cylindrical portion and first attaching means which in the form shown is a lower generally cylindrical portion 118 of reduced diameter having internal threads (not shown). Receptacle 120 has second attaching means in the form of a generally cylindrical mouth portion 124 on which are formed external threads 124 which are adapted to be threadedly engaged with threads contained in section 118.

In the form shown in FIG. 11, the column 128 is generally cylindrical and has a lower portion 130 which has externally positioned threads 132. The underlying receptacle 134 has an upper generally cylindrical neck portion which has internal threads adapted to mate with threads 132.

FIG. 12 illustrates a column 140 which has a generally cylindrical lower section 142 provided with a slot which has a generally vertically oriented portion 144 connected to a generally horizontally oriented portion 146. A similar second slot (not shown) is positioned generally diametrically opposite to slot 144, 146. Receptacle 150 has a mouth provided with a pair of generally diametrically opposed generally radially outwardly projecting lugs or pins 152, 154 which are adapted to be received within the two slots of lower portion 142 in order to demountably secure the receptacle 150 to the column 140.

In the embodiment shown in FIG. 13, the column 158 has a pair of generally downwardly depending hook-like members 160, 162. The receptacle 164 has a pair of upwardly directed tabs 166, 170 which respectively, have openings 168, 172 within which hook-like members 160, 162, respectively, are received. The hook-like members 160, 162 are preferably resiliently deformable and have their free ends pointing generally radially outwardly.

In the embodiment shown in FIG. 14, the column 176 has a pair of downwardly depending tabs 178, 180 which have, respectively, openings 182, 184. The receptacle 186 has a pair of generally upwardly and outwardly directed hook-like members 188, 190 which are adapted to be received within openings 182, 184.

While in the foregoing embodiments, the columns and receptacles may be made of any suitable inert material possessing adequate strength, among the preferred materials are glass, plastics such as polyethylene, polypropylene, and polyvinychloride, for example. The economics of these materials are such that a disposable product may be produced. The trunions may be made of stainless steel, for example.

In the practice of this invention virtually all liquid chromagography support materials and equivalents thereof may be employed as the chromatography bed material. Examples of suitable materials are beads for gel filtration (permeation), beads and particles of plastic resin or cellulose for ion exchange chromatography and silica gel particles.

It will be appreciated that in the foregoing embodiments the column-receptacle assemblies are so designed as to fit into a centrifuge rotor in such fashion that the receptacle "hangs down" both under the influence of gravity when the rotor is at rest and under the influence of a centrifugal force field.

In the second group of embodiments of the present invention, apparatus and method adapted for continuous column centrifugal chromatography is provided.

Figure 15:
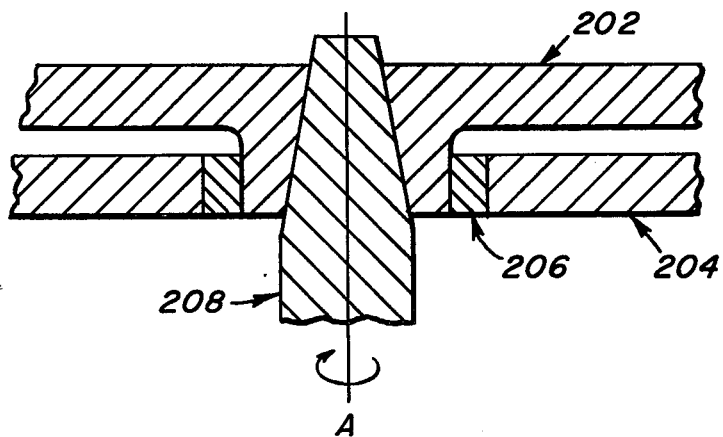
FIG. 15 is a schematic cross-sectional illustration showing means for effecting coordinated rotation of one embodiment of the automated system of the present invention.

As is shown in FIG. 15, a column supporting rotor 202 is fixedly secured to a drive shaft 208 and a collector rotor 204 is secured to a lower extension of the column rotor with an interposed bearing 206. This arrangment results in rotation of the drive shaft 208 about its longitudinal axis A providing synchronized relative rotation of the column rotor 202 and collector rotor 204. This embodiment provides direct securement of the column rotor 202 to the drive shaft 208.

Figure 16:
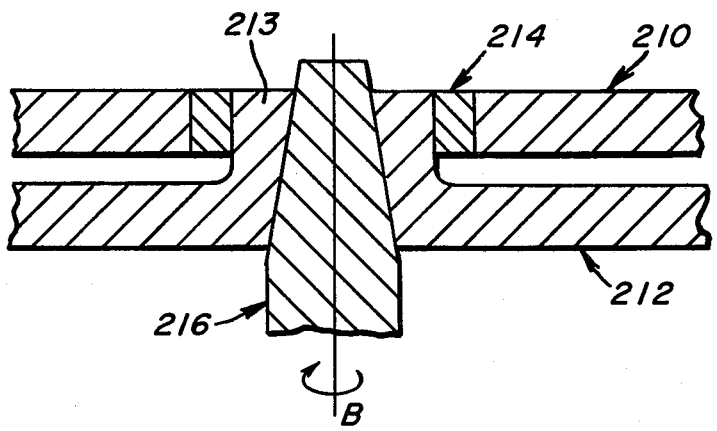
FIG. 16 is a schematic cross-sectional illustration showing another means of effecting coordinated rotation in an automated embodiment of the invention.

In the embodiment shown in FIG. 16, the collector rotor 212 is secured directly to drive shaft 216 which rotates about its longitudinal axis B. The column rotor 210 is secured to an upward extension of hub 213 of the collector rotor 212 with an interposed bearing 214. As a result, synchronized rotation of the collector rotor 212 and column rotor 210 about axis B are provided.

Figure 17:
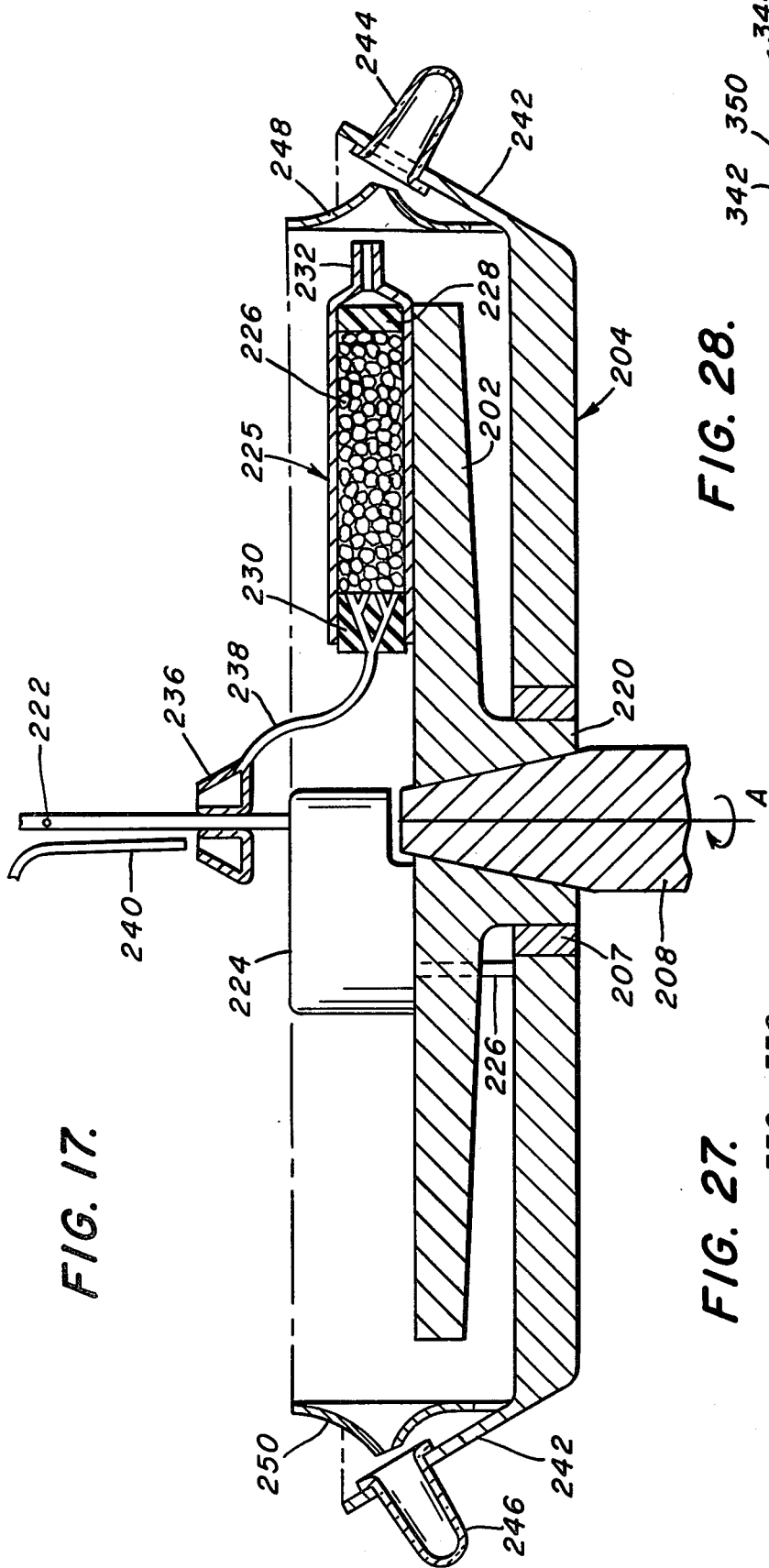
FIG. 17 is a schematic cross-sectional illustration of an automated embodiment of the invention.

Referring now to FIG. 17 there is shown one preferred embodiment of the present invention. In this embodiment the column rotor 202 is fixedly secured to the drive shaft 208 which rotates about axis A and the collector rotor 204 is directly secured to the hub 220 of column rotor 202 through bearing 207. The drive shaft 208 is rotated by a suitable motor with or without interposed speed reducing transmission means (not shown). In a preferred embodiment the drive shaft will rotate at about 100 rpm to about 2000 rpm.

A post member 222 is preferably substantially coaxial with axis A and rotates thereabout. The post member 222 is through speed reducer 224 which is secured to column rotor 202 and contains suitable gearing (not shown) connected to stub shaft 226 which is secured to collector rotor 204. This serves to provide coordinated relative movement of rotors 202, 204 and post member 222. At least one chromatographic column 225 is provided with a chromatographic bed 226, a porous disc 228, a stopper 230 at one end and a discharge outlet 232 at the other.

Referring still to FIG. 17, a reservoir 236 which is annular in shape and upwardly open and rigidly secured to post 222 for rotation therewith is adapted to receive liquid from nonrotating tube 240. Liquid delivered from nonrotating tube 240 will enter reservoir 236 and by means of tube 238 under the influence of centrifugal force and gravity deliver liquid into stopper 230 and from there into the bed 226. It will be appreciated, therefore, that as drive shaft 208 rotates, the liquid will be processed through the column 225 and the elution solution will be discharged through opening 232.

Considering still FIG. 17, a preferred form of collector rotor 204 will now be discussed. The outer portion of the collector rotor 204 has a generally upwardly and angularly outwardly directed ring 242 secured thereto. Mounted within the rings are a series of receptacles 244, 246 (only two of which are shown in FIG. 17). It is understood that a substantially continuous circumferential array of receptacles would be provided so as to permit substantially continuous receipt of eluted liquid from the discharge opening 232. In order to facilitate efficiency of fluid transfer from discharge opening 232 into the array of tubes 244, 246 and the remaining tubes (not shown) a series of funnels 248, 250 are interposed between the column opening 232 and the receptacles.

Referring to FIGS. 18 through 24, certain preferred constructions of liquid transfer reservoirs will now be considered. In the embodiment shown in FIGS. 18 and 19 the reservoir 252 is generally frustoconical in shape, has a single discharge tube 254 and a liquid receiving opening 256. It has a single interior chamber 258

Figure 21:
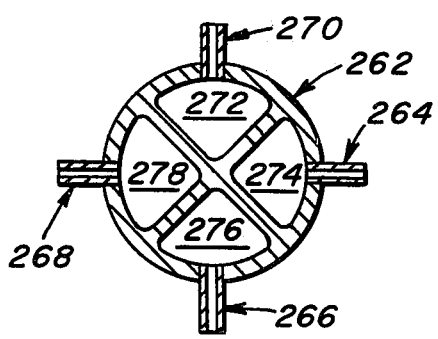
FIG. 21 is a cross-sectional illustration of the reservoir of FIG. 20 taken through 21-21.
Figure 20:
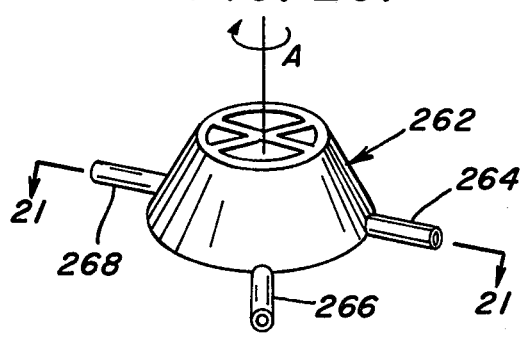
FIG. 20 is a prespective illustration of another form of reservoir usable in an automated embodiment of the present invention.

In the embodiment shown in FIGS. 20 and 21, the reservoir 262 also has a frustoconical configuration and is provided with a series of interior liquid receiving or storage chambers 272, 274, 276, 278. Four outlet tubes 264, 266, 268, 270 are each associated with an interior liquid receiving or storage chamber 272, 274, 276, 278 for supplying liquid to a column.

Figure 23:
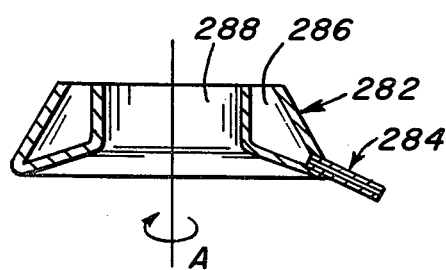
FIG. 23 is a cross-sectional illustration of the reservoir shown in FIG. 22 taken through 23-23.
Figure 22:
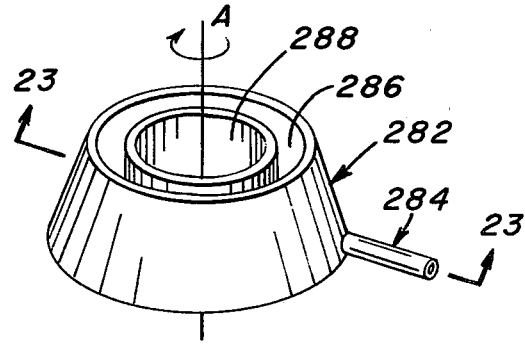
FIG. 22 is a perspective illustration of another form of liquid reservoir adapted for use with an automated embodiment of the present invention.

In the embodiment shown in FIGS. 22 and 23, the reservoir 282 has a single outlet tube 284 and is provided with an annular storage chamber 286 surrounding an interior opening 288.

Figure 25:
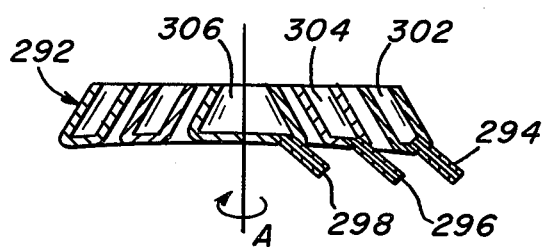
FIG. 25 is a cross-sectional illustration of the reservoir shown in FIG. 24 taken through 25-25.
Figure 24:
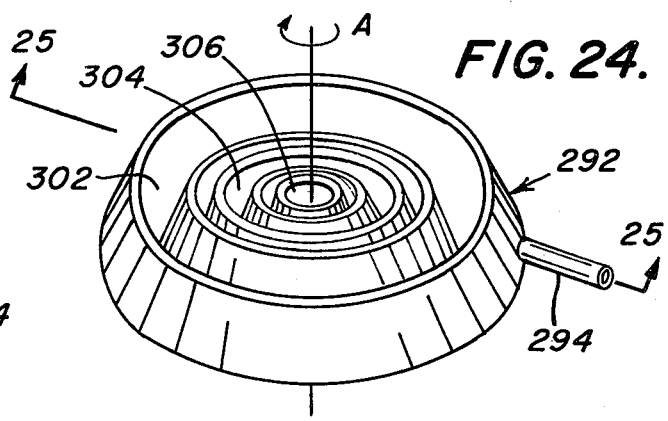
FIG. 24 is a perspective view of another form of liquid reservoir of the present invention.

In the embodiment shown in FIGS. 24 and 25, the reservoir 294 has three chambers 302, 304, 306 and associated discharge tubes 294, 296, 298 respectively. The chamber 306 is generally frustoconical in shape and the other chambers 302, 304 are annular.

It will be appreciated from the foregoing that it is preferred that the number of chambers in the reservoir equal the number of supply tubes emerging therefrom to provide liquid to columns.

Figure 26:
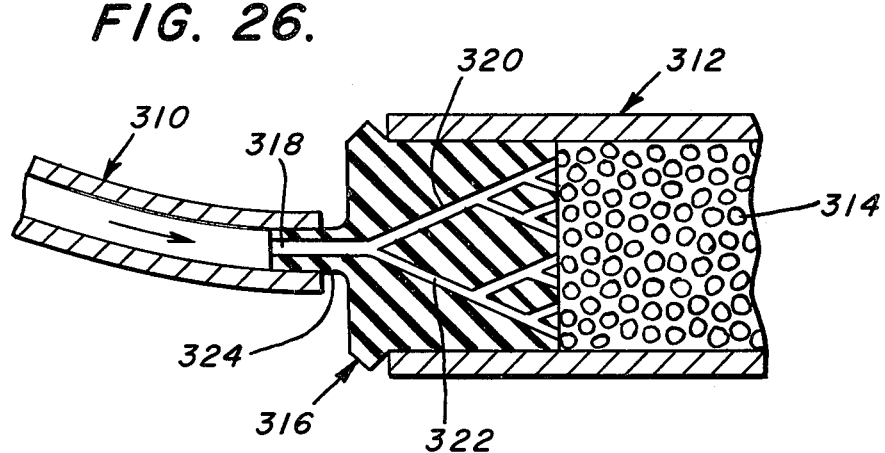
FIG. 26 is a fragmentary cross-sectional detail showing a unique form of stopper member employed in connection with the column.

FIG. 26 shows a preferred form of stopper which facilitates even disbursement of liquid within a column. A supply tube 310 delivers liquid to a column 312 which has a column bed 314 and a stopper 316. The stopper 316 has a main passageway 318 which is in communication with the tube 310 and a number of branch passageways 320, 322 preferably of reduced size with respect to the main passageway 318. In the form shown the stopper has a tubular extension 324 which is received within tube 310.

Figure 27:
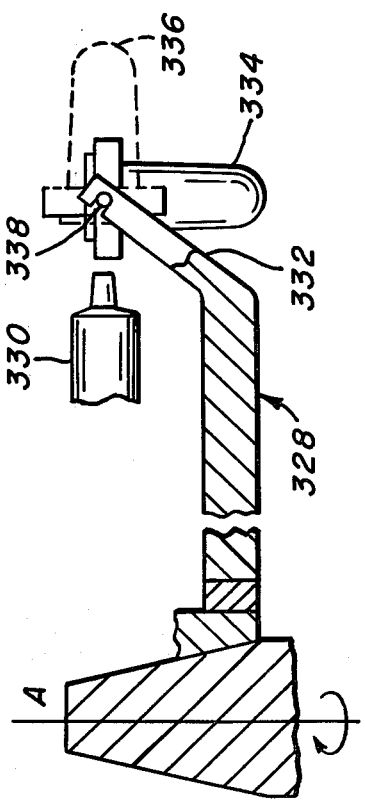
FIG. 27 illustrates a form of collection or receptacle tube mounting of the present invention.
Figure 19:
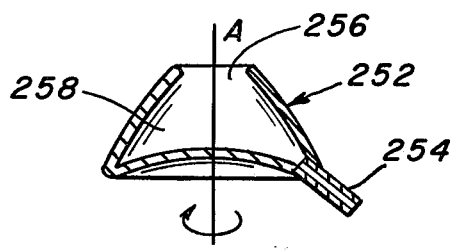
FIG. 19 is a cross-sectional illustration of the reservoir shown in FIG. 18 taken through 19-19.
Figure 18:
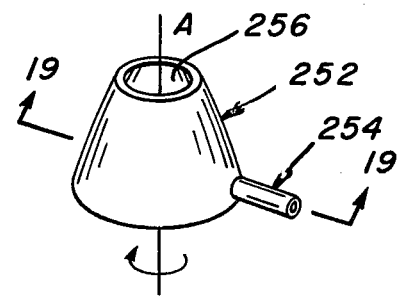
FIG. 18 illustrates a form of liquid reservoir employable in an automated version of the present invention.

Referring now to FIG. 27 there is shown a modified form of collector system. Collector rotor 328 has annular outer ring 332. A column 330 is adapted to discharge material into a receptacle 334. The receptacle at rest 334 is generally vertically oriented, but under the influence of centrifugal force is adapted to assume the dotted position shown at 336 by pivoting about trunion pins 338 (only one shown) which project outwardly from opposite sides of receptacle 334 and are rotatably received within ring 332, as by grooves therein. The pivot pins 338 may take the form of a pair of outwardly projecting lugs provided on a ring which supports a receptacle upper flange. In a preferred form, the trunion pins 338 or other pivot means will be positioned within the upper one-third of the longitudinal axial extent of receptacle 334 to facilitate efficient rotation.

Figure 28:
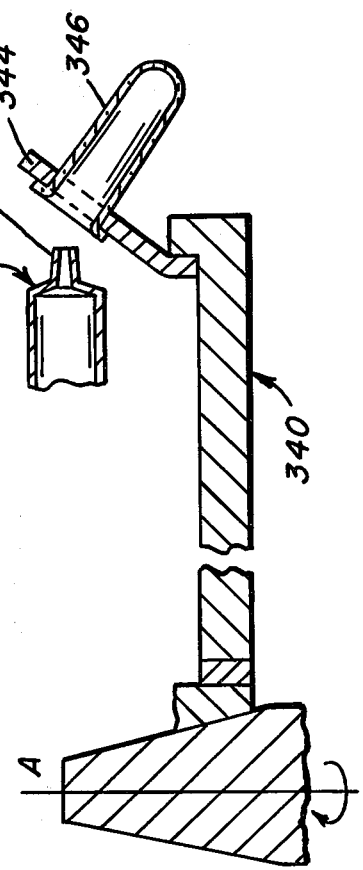
FIG. 28 is a cross-sectional illustration of another form of collection or receptacle tube mounting of the present invention.

FIGS. 28 through 39 shown certain preferred means for distributing liquid from a column to a series of receptacle tubes. In FIG. 28, the rotor 340 is provided with an angularly disposed annular ring 344 within which is mounted a receptacle 346 having its longitudinal axis directed generally angularly upwardly and inwardly. The column 342 has a discharge opening 350 which is generally aligned with the opening in the receptacle 346.

Figure 29:
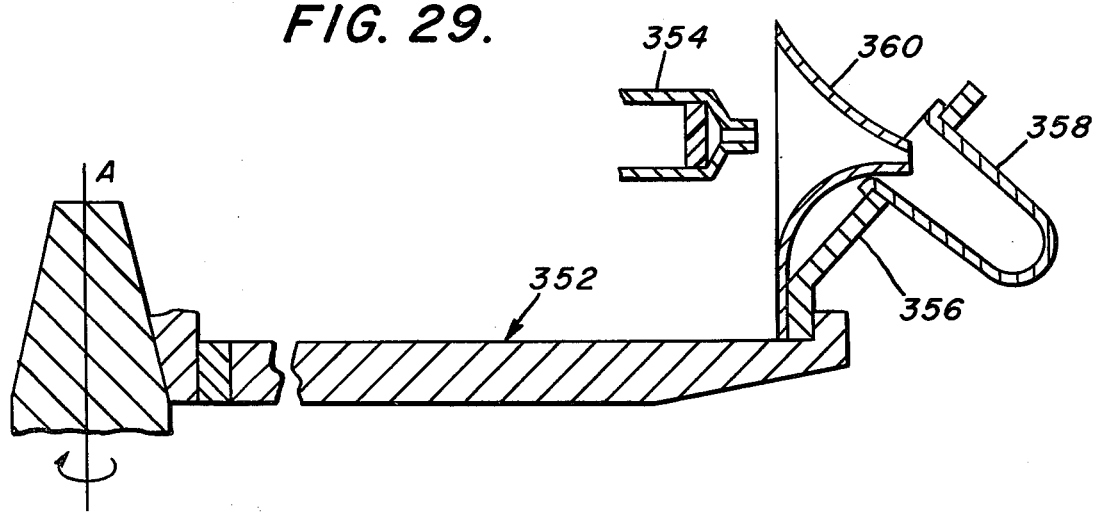
FIGS. 29 and 30 are fragmentary cross-sectional illustrations of embodiments of the invention providing a funnel effect to improve efficiency of liquid transfer to collection tubes.

In the embodiment shown in FIG. 29, the collector rotor 352 is adapted to receive liquid from column 354. An outer annular ring 356 has a lower generally vertically oriented portion and an upper angularly outwardly directed portion which has a recess which supports receptacle 358. A funnel member 360 has its lower end mounted adjacent the annular ring 356, its receiving end aligned with the column 354 and its discharge end inserted into receptacle 358.

Figure 30:
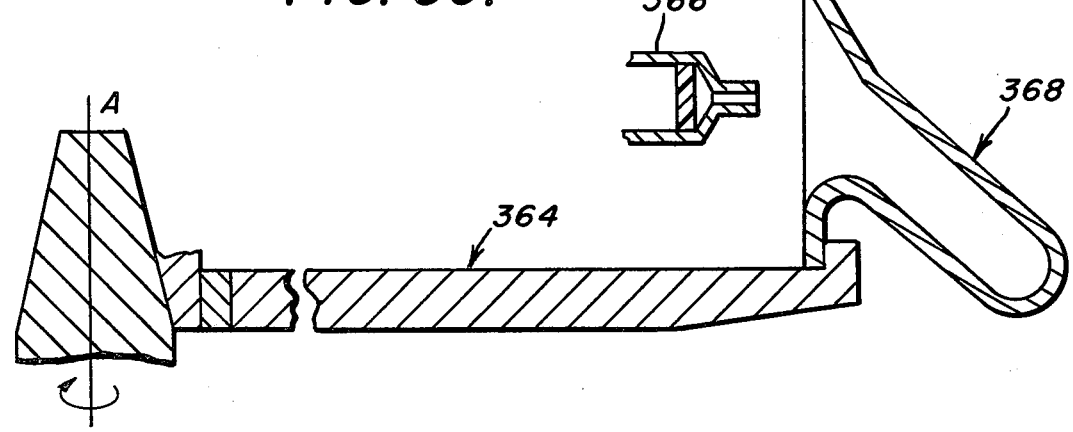

In the embodiment shown in FIG. 30, the rotor 364 is adapted to receive liquid from column 366. The rotor 364 is provided with a series of receptacles 368 (one shown) which have an outwardly diverging mouth which serves as a funnel to improve efficiency of transfer of liquid into the receptacle 368.

Figure 31:
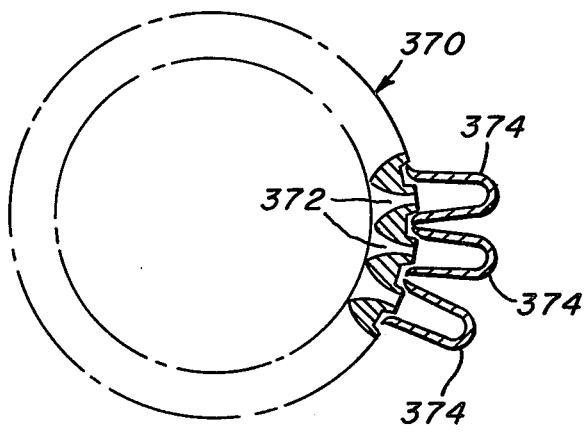
FIG. 31 is a partial cross-sectional illustration of a form of funnel plate adapted to facilitate transfer of fluid to the collection tubes.

Referring to FIG. 31, there is shown partially in section, as viewed from above an annular funnel plate 370 which is preferably mounted on the collection rotor and is provided with a series of openings 372 which converge generally radially outwardly and are aligned with a series of receptacles 374. In this fashion all liquid being discharged toward the funnel plate will be received within an opening 372 and distributed to an adjacent receptacle 374. It will be appreciated that while only three receptacles 374 have been shown in use, a receptacle would be preferably provided for each opening 372.

Figure 32:
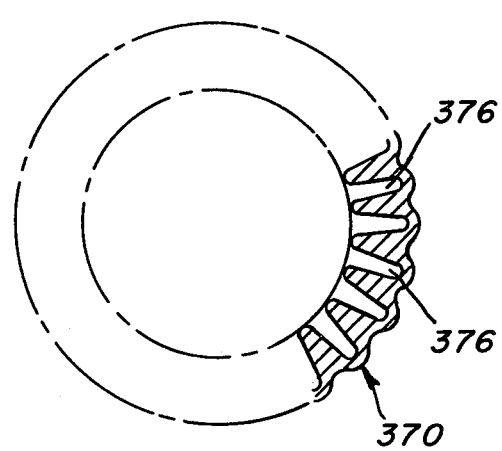
FIG. 32 is a partial cross-sectional illustration of a form of funnel plate having integral collecting tubes.

In the embodiment shown in FIG. 32, the annular ring which is mounted on the collection rotor is provided with a series of receptacles integrally formed within the ring. It is noted that the receptacles have their widest opening adjacent the inner circumference of the ring. In order to minimize undesired spillage, the ring slopes downwardly and outwardly from its inner extremity. As a result, the receptacles would slope downwardly away from their mouths to the closed end so that they might retain fluid under the influence of both centrifugal and gravity forces.

Figure 33:
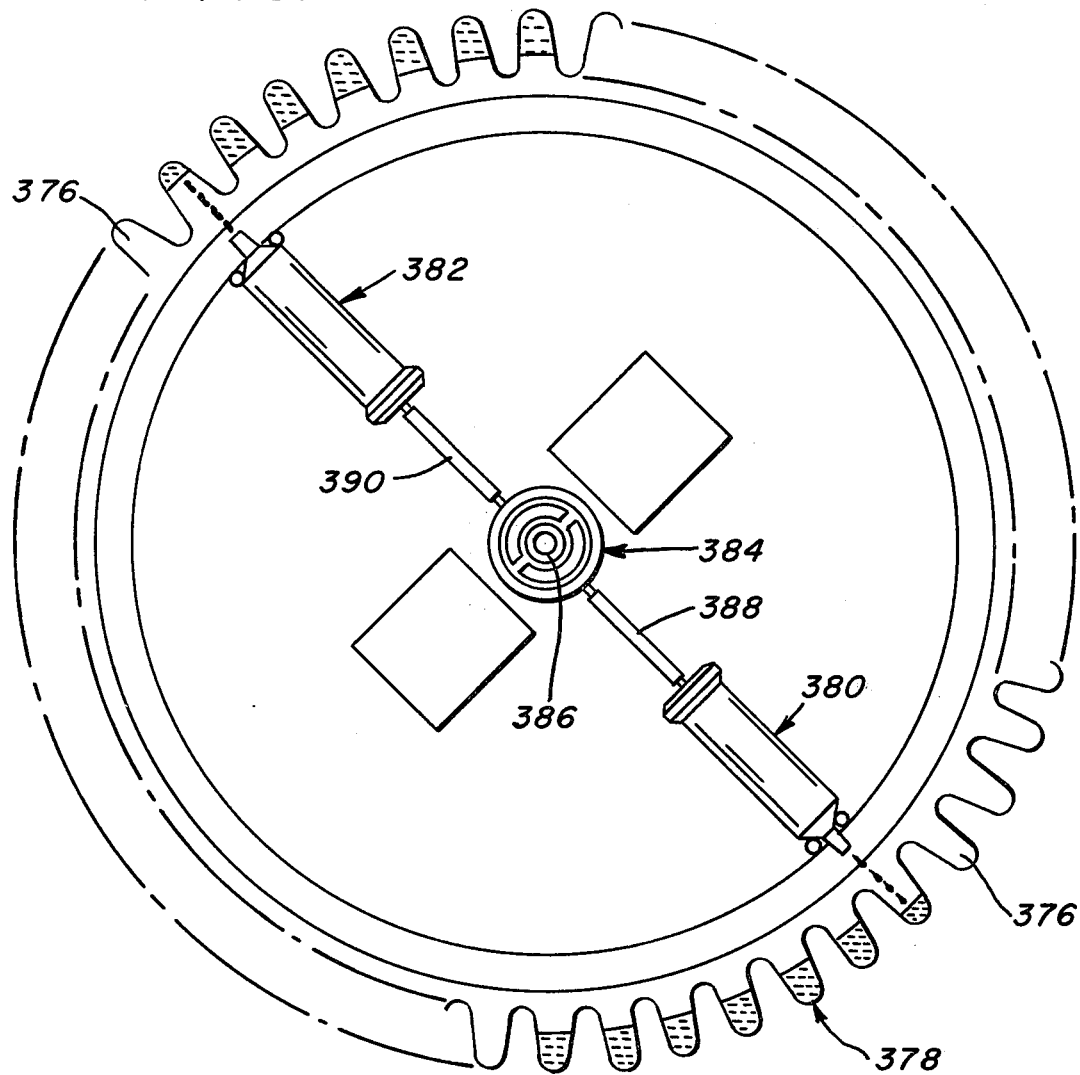
FIG. 33 is a partially schematic top plan view illustrating transfer from two columns to an adjacent funnel and collection tube plate.

The ring of FIG. 32 is shown in FIG. 33 as well. In this embodiment the system has two columns 380 and 382 which have discharge outlets generally radially opposed from each other. Reservoir 384 is mounted on post 386 and supplies liquid to columns 380, 382, respectively, through tubes 388, 390. As the columns rotate they sequentially fill the openings 376.

If desired, as in the FIG. 33 embodiment, for example, the columns may be subjected to rotation about their longitudinal axis by any means either coordinated with main drive shaft rotation as by appropriate reduction gears, for example, or any form of independent means. Axial rotation of the columns can result in even greater resolution as a result of the rotation which tends to conteract the Coriolis force. This resistance to the Coriolis force causes the liquid to flow down the column generally parallel to the tube's longitudinal axis rather than at an angle with respect thereto. This results in more uniform travel of the transverse zones or bands of molecules downwardly. Rotation of several revolutions per minute would be adequate for this purpose.

In the method of this embodiment of the invention continuous column centrifugation chromatography is provided by applying a centrifugal force to one or an array of columns. Synchronized relative movement of an array of associated receptacles is effected in order that the receptacles may receive liquid discharged from the columns. A continuous supply of liquid is provided to the centrifuge columns through reservoir and supply means.

It will be appreciated that it will generally be advantageous to employ with the automated version of the invention, reservoir means. The system may, however, if desired, be provided with a rotatable coupling to secure a stationary liquid supply tube to a rotating tube connected to the columns.

It will be appreciated that the present invention is adapted for a wide range of uses including clinical chemical research and industrial uses. Examples of advantageous uses include:

(a) removing salts and other small molecules from proteins in biological fluids such as blood serum and cerebrospinal fluid;
(b) removing unbound small molecules, such as steroids, from larger molecules, such as antibody proteins, in diagnostic tests such as radio-immuno assay procedures;
(c) separating large proteins, large polysaccharide, and large nucleic acids, from small molecules of these types of clinical samples, prior to or during diagnostic testing;
(d) separate proteins such as serum proteins from salts;
(e) separate proteins from steroids and other small hormones, including small peptide hormones;
(f) separate proteins from drug molecules;
(g) assay the binding of drugs to proteins;
(h) assay the binding of hormones to proteins;
(i) separate proteins of various sizes and/or shapes from each other;
(j) separate nucleic acid molecules from salts; and
(k) separate nucleic acid molecules of differing sizes from each other—for example, DNA fragments of different lengths.

It will be appreciated that the present invention has provided an efficient means for obtaining the full benefits of liquid-solid column centrifuge chromatography in a rapid fashion without undesired dilution of the specimens.

Whereas particular embodiments of the invention have been described above for purposes of illustration, it will be evident to those skilled in the art that numerous variations of the details may be made without departing from the invention as defined in the appended claims.

We claim:

1. Column centrifugation chromatography apparatus comprising
   column rotor means for supporting and applying centrifugal force to a plurality of circumferentially spaced nonhelical centrifugation columns,
   said centrifugation columns being generally radially oriented,
   collector rotor means for collecting material discharged from said columns,
   a plurality of receptacles secured to said collector rotor means for receiving liquid discharged from said column,
   said receptacles disposed radially outwardly of said columns,
   power means for establishing synchronized relative movement of said column rotor means and said collector rotor means,
   said column rotor means and said collector rotor means being mounted for substantially coaxial rotation, and
   distribution means for supplying liquid to said columns while said column rotor means is subjected to said movement.

2. The column centrifugation chromatography apparatus of claim 1 wherein
   at least one of said column rotor means and said collector rotor means being secured to a drive shaft, and
   said power means including motor means for rotating said drive shaft.

3. The column centrifugation chromatography apparatus of claim 1 wherein
   said distribution means including reservoir means mounted for rotation with said column rotor means and
   means connecting said reservoir with said columns.

4. The column centrifugation chromatography apparatus of claim 3 wherein
   said reservoir means are supported by post means disposed generally on the axis of rotation of said column rotor means.

5. The column centrifugation chromatography apparatus of claim 3 wherein
   said reservoir means has an open upper portion for receipt of liquid, and
   supply conduit means for delivering said liquid to said reservoir.

6. The column centrifugation chromatography apparatus of claim 3 wherein
   said reservoir means being closed, and
   supply conduit means sealingly connected to said reservoir and delivering liquid thereto.

7. The column centrifugation chromatography apparatus of claim 3 wherein
said reservoir means has a unitary storage chamber.

8. The column centrifugation chromatography apparatus of claim 3 wherein
said reservoir means having a number of chambers.

9. The column centrifugation chromatography apparatus of claim 3 wherein
said reservoir means has a generally annular chamber.

10. The column centrifugation chromatography apparatus of claim 8 wherein
said reservoir means has a number of annular generally concentric chambers.

11. The column centrifugation chromatography apparatus of claim 1 wherein
said distribution means include tube means for delivery of liquid to said columns, and
stopper means in communication with said tube means and said columns.

12. The column centrifugation chromatography apparatus of claim 11 wherein
said stopper means include a stopper having one passageway in communication with said tube means, and
said passageway branching into a number of subpassageways for discharge of said liquid to several portions of the interior of said column.

13. The column centrifugation chromatography apparatus of claim 1 wherein
said collector rotor means have an annular array of said receptacles.

14. The column centrifugation chromatography apparatus of claim 1 wherein
said receptacles are fixedly mounted with their openings facing generally upwardly and radially inwardly with respect to the center of said collector rotor means.

15. The column centrifugation chromatography apparatus of claim 14 wherein
said receptacles have mouths which diverge generally
radially inwardly with respect to the longitudinal axis of said receptacles.

16. The column centrifugation chromatography apparatus of claim 1 wherein
funnel means are interposed between said columns and said receptacles for facilitating efficient transfer of liquid from said columns to said receptacles.

17. The column centrifugation chromatography apparatus of claim 16 wherein
said funnel means include an annular member having a plurality of generally radially oriented openings, and
said openings diverge generally radially inwardly.

18. The column centrifugation chromatography apparatus of claim 1 wherein
said receptacles are formed integrally within an annular member.

19. The column centrifugation chromatography apparatus of claim 1 wherein
said receptacles are rotatably secured to said collector rotor means, whereby application of centrifugal force thereto will result in the receptacles rotating generally outwardly and upwardly.

20. The centrifugation chromatography apparatus of claim 1 including
said column rotor means having means for supporting chromatography columns, and
means for effecting rotation of said columns about their longitudinal axis.

21. A method of continuous column centrifugation chromatography comprising
providing an annular array of generally radially oriented columns,
applying a centrifugal force to said array of columns through rotation of said array,
effecting synchronized relative movement of an array of receptacles positioned generally radially outwardly of said columns to receive liquid discharge from said columns, and
supplying on a continuous basis liquid to said centrifuge columns.

22. The method of chromatography of claim 21 including
providing chromatographic bed material in said columns, and
removing effluent from said columns on a substantially continuous basis.

* * * * *

UNITED STATES PATENT AND TRADEMARK OFFICE
CERTIFICATE OF CORRECTION

PATENT NO. : 4,422,941

DATED : December 27, 1983

INVENTOR(S) : Maurice H. Vaughan, Jr. and Klaus B. Andersen

It is certified that error appears in the above-identified patent and that said Letters Patent is hereby corrected as shown below:

Column 2, line 58, "meansreceptable" should be --means-receptacle--.

Column 2, line 63, "rotarably" should be --rotatably--.

Column 2, line 68 to column 3, line 1, "established" should be --establish--.

Column 3, line 3, "provided" should be --provide--.

Column 5, line 4, "column2" should read --column 2--.

Column 6, line 25, "liqud" should be --liquid--.

Column 10, line 31, "39" should be --30--.

Column 10, line 31, "shown" should be --show--.

Signed and Sealed this

Seventh Day of August 1984

[SEAL]

Attest:

GERALD J. MOSSINGHOFF

Attesting Officer

Commissioner of Patents and Trademarks